United States Patent

Jinnouchi

(10) Patent No.: US 11,058,360 B2
(45) Date of Patent: Jul. 13, 2021

(54) PULSE MEASUREMENT DEVICE, PULSE MEASUREMENT METHOD AND NON-TRANSITORY COMPUTER READABLE MEDIUM

(71) Applicant: RENESAS ELECTRONICS CORPORATION, Tokyo (JP)

(72) Inventor: Masaki Jinnouchi, Tokyo (JP)

(73) Assignee: RENESAS ELECTRONICS CORPORATION, Tokyo (JP)

(*) Notice: Subject to any disclaimer, the term of this patent is extended or adjusted under 35 U.S.C. 154(b) by 646 days.

(21) Appl. No.: 15/895,462

(22) Filed: Feb. 13, 2018

(65) Prior Publication Data

US 2018/0279957 A1    Oct. 4, 2018

(30) Foreign Application Priority Data

Mar. 30, 2017    (JP) .............................. JP2017-067338

(51) Int. Cl.
*A61B 5/024* (2006.01)
*A61B 5/00* (2006.01)

(52) U.S. Cl.
CPC .......... *A61B 5/721* (2013.01); *A61B 5/02416* (2013.01); *A61B 5/02438* (2013.01); *A61B 2562/0219* (2013.01)

(58) Field of Classification Search
None
See application file for complete search history.

(56) References Cited

U.S. PATENT DOCUMENTS 5,697,374 A    12/1997 Odagiri et al.
2003/0009091 A1*  1/2003 Edgar, Jr. ............. A61B 5/7207
                                                    600/323
(Continued)

FOREIGN PATENT DOCUMENTS

JP    07-227383 A    8/1995
JP    2014-054417 A    3/2014
(Continued)

OTHER PUBLICATIONS

Japanese Notice of Reasons for Refusal issued in corresponding Japanese Patent Application No. 2017-067338, dated Aug. 18, 2020, with English translation.

(Continued)

*Primary Examiner* — Kaylee R Wilson
*Assistant Examiner* — Jay B Shah
(74) *Attorney, Agent, or Firm* — McDermott Will & Emery LLP

(57) ABSTRACT

It is possible to measure a pulse rate correctly, when a body moves. A frequency analysis unit 13 generates a pulse wave frequency signal by converting pulse wave detection signals detected by a light sensor 20 into a frequency domain signal from time domain signals. A body motion level determination unit 14 determines a body motion level of a subject based on acceleration detection signals output by an accelerometer 21. A peak detection unit 15 detects a peak of spectrum intensity in the pulse wave frequency signal within a peak searching range, which varies depending on the determined body motion level. A pulse calculation processing unit 16 generates pulse information based on a frequency position of the peak detected by the peak detection unit 15.

17 Claims, 11 Drawing Sheets

(56) References Cited

U.S. PATENT DOCUMENTS

| | | | |
|---|---|---|---|
| 2015/0173627 A1 | 6/2015 | Fujii et al. | |
| 2015/0302158 A1* | 10/2015 | Morris | G06K 9/00563 |
| | | | 702/19 |
| 2015/0335934 A1* | 11/2015 | Flynn | A47B 65/20 |
| | | | 434/365 |
| 2016/0051158 A1* | 2/2016 | Silva | A61B 5/721 |
| | | | 600/479 |
| 2016/0089086 A1* | 3/2016 | Lin | A61B 5/721 |
| | | | 600/479 |
| 2016/0235371 A1 | 8/2016 | Hiroshima et al. | |
| 2016/0367158 A1* | 12/2016 | Samadani | A61B 5/7278 |

FOREIGN PATENT DOCUMENTS

| | | |
|---|---|---|
| JP | 2014-094043 A | 5/2014 |
| JP | 2016-146933 A | 8/2016 |
| WO | 2015/129557 A1 | 9/2015 |
| WO | WO-2015129557 A1 * | 9/2015 ............. A61B 5/721 |

OTHER PUBLICATIONS

Japanese Notice of Reasons for Refusal issued in corresponding Japanese Patent Application No. 2017-067338, dated Mar. 16, 2021, with English translation.

* cited by examiner

PULSE MEASUREMENT DEVICE, PULSE MEASUREMENT METHOD AND NON-TRANSITORY COMPUTER READABLE MEDIUM

CROSS-REFERENCE TO RELATED APPLICATIONS

This application is based upon and claims the benefit of priority from Japanese patent application No. 2017-067338, filed on Mar. 30, 2017, the disclosure of which is incorporated herein in its entirety by reference.

BACKGROUND

The present disclosure relates to a pulse measurement device, a pulse measurement method, and a non-transitory computer readable medium, for example, relates to a pulse measurement device, a pulse measurement method, and a non-transitory computer readable medium storing a program for measuring a pulse rate of a subject based on detected pulse wave signals of the subject.

Japanese unexamined patent publication No. 2016-146933 discloses a pulse rate meter using a light sensor including a light emitter such as LED (light emitting diode) and a photodetector such as a phototransistor or a photodiode. In the pulse rate meter disclosed in Japanese unexamined patent publication No. 2016-146933, a Fourier Transform process is performed upon detection signals acquired from the light sensor. Japanese unexamined paten publication No. 2016-146933 discloses that a peak is detected in a spectrum obtained by Fourier Transform and a pulse rate is calculated from a frequency position of the peak.

SUMMARY

Here, when a pulse rate meter measures a pulse rate while a user is exercising, frequency components due to body motions of the user are superimposed on detection signals of the light sensor or the like. In the pulse rate meter disclosed in Japanese unexamined patent publication No. 2016-146933, in the Fourier-transformed spectrum, spectrum intensity which is the maximum within a predetermined searching range is detected as a peak. In the pulse rate meter disclosed in Japanese unexamined patent publication No. 2016-146933, a frequency component due to the body motion is possibly detected as the peak when the frequency component due to the body motion is greater than frequency components of the pulse wave. In this case, it is impossible to measure the pulse rate correctly.

Other problems of the related art and new features of the present disclosure will become apparent from the following descriptions of the specification and attached drawings.

According to an example aspect, a pulse measurement device comprises, a pulse wave frequency information generation module that generates a pulse wave frequency signal which is obtained by converting pulse wave detection signals detected by the light sensor or the like into a frequency domain signal from time domain signals, and a peak detection module that detects a peak of spectrum intensity in the pulse wave frequency signal, and wherein the peak detection module varies a peak searching range from which the peak is detected according to a body motion level of a subject.

According to the above example aspect, it is possible to measure a pulse rate correctly even if the subject moves.

BRIEF DESCRIPTION OF THE DRAWINGS

The above and other aspects, advantages and features of the present disclosure will be more apparent from the following description of certain embodiments thereof taken in conjunction with the accompanying drawings, in which.

DETAILED DESCRIPTION

Prior to giving explanations of embodiments, matters which the inventor has considered are explained. In general, in calculation of a pulse value in a frequency analysis such as Fast Fourier Transform or Wavelet Transform, in a frequency-converted spectrum, a frequency position at which spectrum intensity is the maximum in a preset pulse detection range is identified. The pulse detection range is set, for example, 30 bpm (beat per minute) to 230 bpm.

Figure 11:
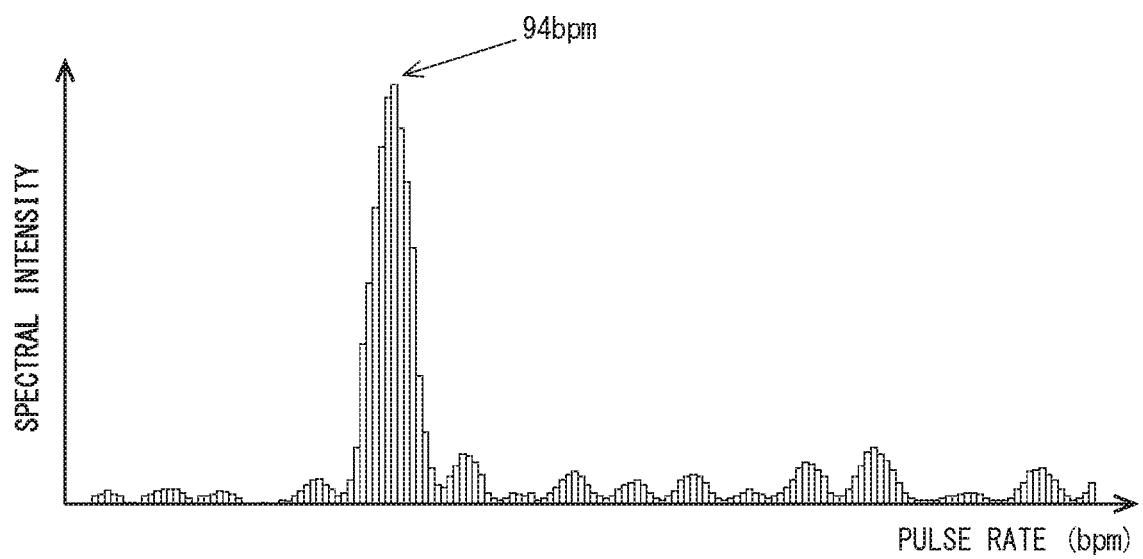
FIG. 11 is a graph showing a frequency spectrum of detection signals of a pulse wave when a body does not moves.

FIG. 11 shows a frequency spectrum of detection signals of a pulse wave. The frequency spectrum shown in FIG. 11 is obtained, for example, by performing Fast Fourier Transform on detection signals of a pulse wave. When the subject is in a resting state, a spectrum of a frequency corresponding to a pulse rate becomes the maximum in the detection signals of the pulse rate.

Accordingly, by identifying the frequency at which the spectrum intensity becomes the maximum within a range of a pulse detection range, for example, from the frequency spectrum shown in FIG. 11, and converting the identified frequency into a pulse value, a result of measurement of the pulse rate is obtained. In FIG. 11, a peak appears at a frequency corresponding to the pulse value 94 bpm, and the result of measurement of the pulse rate can be obtained by detecting this peak.

Figure 12:
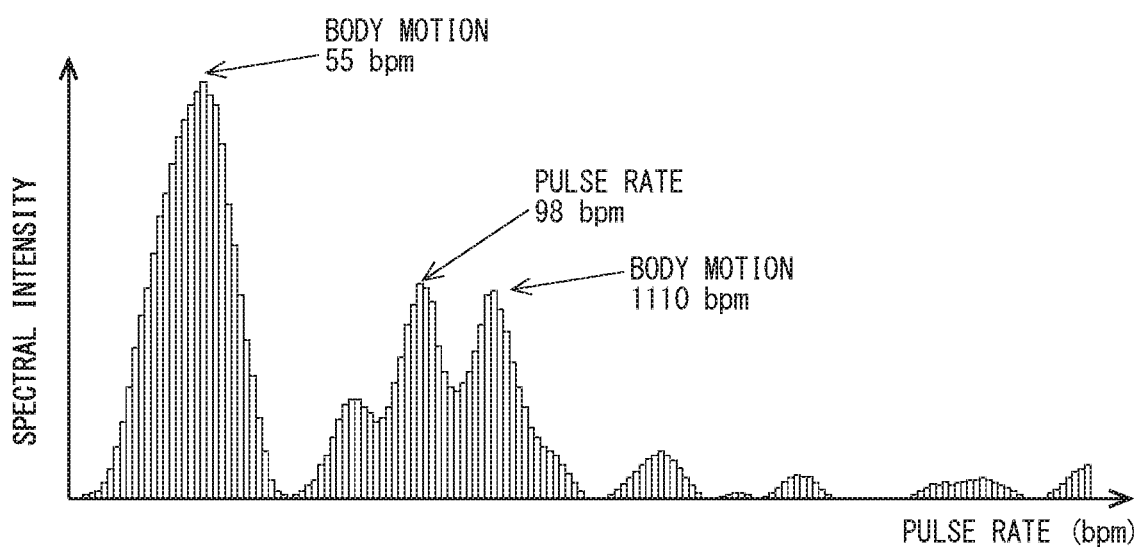
FIG. 12 is a graph showing a frequency spectrum of detection signals of a pulse wave when a body moves.

However, when the subject moves, components other than the pulse wave sometimes appear as noises in the result of the frequency analysis. FIG. 12 shows a frequency spectrum of detection signals of a pulse wave when a body moves. For example, in a case of a wearable pulse monitor attached on a wrist, fluctuations are caused on the detection signals (sensing data) of the pulse wave due to movements of the user, and these fluctuations appear as peaks of spectrum intensity in the frequency analysis. In an example of FIG. 12, in the frequency spectrum of the detection signals of the pulse wave, two peaks (55 bpm and 110 bpm) caused by the body motion appear in addition to a peak (98 bpm) corresponding to the pulse rate. In this case and the like, when a frequency position at which the spectrum intensity becomes the maximum is simply detected, there is a problem that an accurate pulse value cannot be obtained.

As described above, in a case where the pulse value is obtained by a frequency analysis method, if the peak is detected from a whole range of the pulse detection range when the user moves, a peak caused by a body motion noise is sometimes detected as the pulse value erroneously. The body motion noise when the user starts to move tends to be generated strongly at a lower frequency side than the actual pulse value, and thus the pulse value tends to be detected as being low erroneously. Further, when the user who attaches the pulsimeter to himself/herself walks, runs, or the like, if he/she waves his/her arms at a constant cycle, a peak appears at a frequency position corresponding to that cycle, and thus this peak tends to be detected as the pulse rate erroneously. Even if a peak detection window range is set when a body moves, when the range is constant, an erroneous detection cannot be sufficiently prevented when the pulse rate rises sharply at the beginning of a movement, or when the pulse rate falls sharply at the end of a movement.

Hereinafter, embodiments incorporating means for solving the above-described problems will be described in detail with reference to the drawings. For the clarification of the description, some of the following description and the drawings may be omitted or simplified as appropriate. Further, each element shown in the drawings as functional blocks that perform various kinds of processing can be formed of a CPU (Central Processing Unit), a memory, and other circuits in hardware and may be implemented by programs loaded in the memory in software. Those skilled in the art will therefore understand that these functional blocks may be implemented in various ways by only hardware, only software, or a combination thereof without any limitation. Throughout the drawings, the same components are denoted by the same reference symbols and overlapping descriptions will be omitted as appropriate.

The above program can be stored and provided to a computer using any type of non-transitory computer readable medium. Non-transitory computer readable medium include any type of tangible storage medium. Examples of non-transitory computer readable medium include magnetic storage medium (such as floppy disks, magnetic tapes, hard disk drives, etc.), optical magnetic storage medium (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable medium. Examples of transitory computer readable medium include electric signals, optical signals, and electromagnetic waves. Transitory computer readable medium can provide the program to a computer via a wired communication line (e.g. electric wires, and optical fibers) or a wireless communication line.

The present disclosure will be described by dividing it into a plurality of sections or embodiments whenever circumstances require it for convenience in the following embodiments. However, unless otherwise particularly specified, these sections or embodiments may be not irrelevant to one another. One section or embodiment may be related to modifications, applications, details, supplementary explanations, and the like of some or all of the other ones. When reference is made to the number of elements or the like (including the number of pieces, numerical values, quantity, range, etc.) in the following embodiments, the number thereof is not limited to a specific number and may be greater than or less than or equal to the specific number unless otherwise particularly specified and definitely limited to the specific number in principle.

Further, in the following embodiments, components (including operation steps, etc.) are not always essential unless otherwise particularly specified and considered to be definitely essential in principle. Similarly, when reference is made to the shapes, positional relations, or the like of the components or the like in the following embodiments, they will include ones, for example, substantially approximate or similar in their shapes or the like unless otherwise particularly specified and considered not to be definitely so in principle. This is similarly applicable even to the above-described number or the like (including the number of pieces, numerical values, quantity, range, etc.).

First Embodiment

Figure 1:
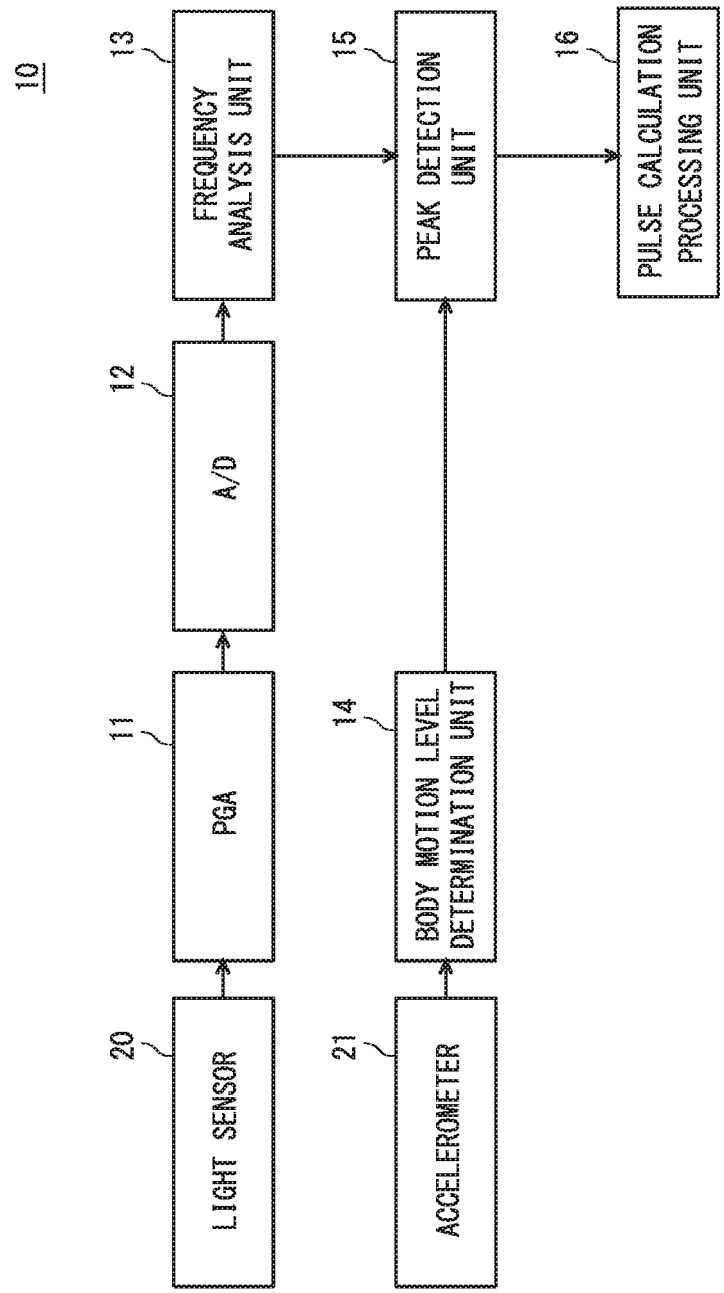
FIG. 1 is a block diagram showing a pulse measurement device according to a first embodiment.

FIG. 1 shows a pulse measurement device according to a first embodiment. A pulse measurement device 10 comprises a PGA (Programmable Gain Amplifier) 11, an AD (analog to Digital) converter 12, a frequency analysis unit 13, a body motion level determination unit (body motion level determination module) 14, a peak detection unit (peak detection module) 15, a pulse calculation processing unit 16, a light sensor 20, and an accelerometer 21. The pulse measurement device 10 is, for example, a wearable device attached to an examinee (subject). The pulse measurement device is configured as, for example, a wristband type device, and is attached to an arm or a wrist of a user. The pulse measurement device 10 is driven, for example, by a battery.

The light sensor 20 detects pulse waves of a user who is a subject. The light sensor 20 comprises, for example, a LED (Light Emitting Diode) and a photodetector. The LED emits light toward apart to be measured where a blood vessel is present in the subject. The subject may be a human being or a non-human animal. For example, the LED periodically emits pulsed light toward the part to be measured in accordance with control of a control unit (not shown). The wave length of the light emitted by the LED is appropriately selected in accordance with a measuring condition and the like. The photodetector receives reflected light reflected from the subject by the light emitted from the LED, and outputs detection signals of the reflected light. For example, a phototransistor, photodiode, or the like can be used as the photodetector. In the detection signals output from the photodetector, the signal intensity varies according to pulsatory motions of the blood vessel. The light sensor 20 outputs the detection signals of the photodetector as pulse wave detection signals.

The PGA 11 amplifies the pulse wave detection signals output from the light sensor 20 to adjust its signal level. The PGA 11 is configured as, for example, a programmable instrumentation amplifier whose gain can be changed. The AD converter 12 converts the pulse wave detection signals whose signal level is adjusted by the PGA 11 into digital signals. For example, a delta-sigma type AD converter is used as the AD converter 12. The frequency analysis unit 13 is a pulse wave frequency information generation module, and generates a pulse frequency signal by converting the pulse wave detection signals into a frequency domain signal from time domain signals. The frequency analysis unit 13 performs, for example, Fast Fourier Transform (FFT) on the pulse wave detection signals of a plurality of data points converted into digital signals to generate the pulse wave frequency signal by performing a frequency analysis on the pulse wave detection signals which are time domain signals.

The accelerometer 21 detects acceleration of the subject. For example, the accelerometer 21 is accommodated in a wristband type device constituting the pulse measurement device 10. The accelerometer 21 outputs acceleration detection signals indicating the result of the detection of the acceleration to the body motion level determination unit 14. For example, an AD converter is built in the accelerometer 21, and the accelerometer 21 outputs the acceleration detection signals which are digital signals. An AD converter may be disposed between the accelerometer 21 and the body motion level determination unit 14 when the accelerometer 21 is a sensor which outputs analog signals.

The body motion level determination unit 14 determines a body motion level of the subject based on the acceleration detection signals output from the accelerometer 21. For example, the body motion level determination unit 14 calculates an average value of the magnitude of the acceleration detection signals within a predetermined period of time, and acquires a temporary body motion level based on the average value. The body motion level determination unit 14 determines the body motion level based on the temporary body motion levels for multiple times. At that time, the body motion level determination unit 14 may determine an average value of the temporary body motion levels for multiple times as the body motion level.

The body motion level includes, for example, a resting state (no body movement) and an active state (having a body movement). Hereinafter, it is assumed that the body motion level determination unit 14 determines, for example, the body motion level in 5 levels according to the magnitude of the motion of the subject. In addition, the body motion level is determined to be higher as the body motion of the subject becomes greater. For example, the body motion level 0 corresponds to a resting state of the subject, and the body motion level 4 corresponds to a state in which the motion of the subject is the greatest.

The peak detection unit 15 searches for a peak of spectrum intensity in the pulse wave frequency signal generated by the frequency analysis unit 13, and detects the peak of the spectrum intensity. In the present embodiment, the peak detection unit 15 varies a peak searching range from which the peak is detected based on the body motion level determined by the body motion level determination unit 14. The peak detection unit 15 searches for the peak, for example, within the peak searching range defined for each of the body motion levels. For example, the peak searching range is set to be narrower as the body motion level becomes higher.

The pulse calculation processing unit 16 is a pulse information generation module, and generates pulse information based on the frequency position of the peak detected by the peak detection unit 15. The pulse information generated by the pulse calculation processing unit 16 is displayed, for example, on a not-shown display unit such as a liquid crystal display. The pulse information may be recoded in a not-shown storage device.

It should be noted that, in the pulse measurement device 10, the PGA 11 and the AD converter 12 may be configured as hardware, for example, disposed inside of a microcomputer unit. At least a portion of functions of the frequency analysis unit 13, the body motion level determination unit 14, the peak detection unit 15, and the pulse calculation processing unit 16 may be realized, in a microcomputer unit having a processor, by the processor operated in accordance with a program.

[Operation Procedure]

Figure 2:
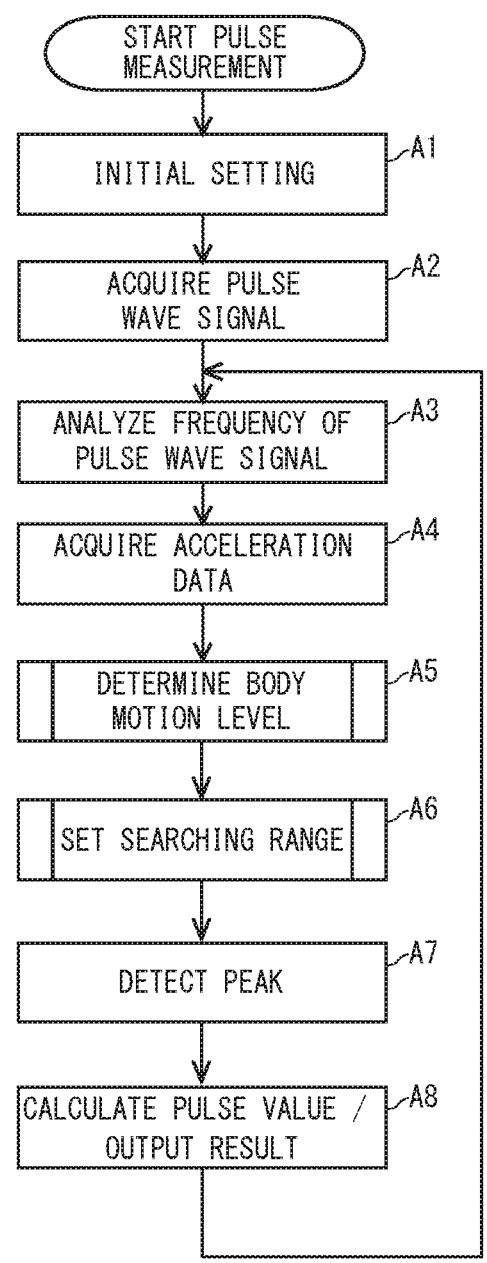
FIG. 2 is a flow chart showing a procedure for measuring a pulse.

FIG. 2 shows a procedure for measuring a pulse. For example, prior to a measurement of the pulse rate, the pulse measurement device 10 carries out initial setting (Step A1). This initial setting includes, for example, calibration of an amount of luminescence of LED in the light sensor 20 and the like. The light sensor 20 emits light, for example, from the LED, receives the reflected light, and outputs pulse wave detection signals to the PGA 11. The light sensor 20 causes the LED to emit light, for example, at a predetermined cycle, and periodically outputs the pulse wave detection signals.

The frequency analysis unit 13 acquires the pulse wave detection signals via the PGA 11 and the AD converter 12 (Step A2). The frequency analysis unit 13 performs, for example, Fast Fourier Transform on the acquired pulse wave detection signals to convert the pulse wave detection signals into a pulse wave frequency signal in the frequency domain (Step A3). The frequency analysis unit 13 executes Step A3, for example, each time the pulse wave detection signals of data points required for Fast Fourier Transform are acquired.

On the other hand, for example, the accelerometer 21 continuously outputs acceleration detection signals. The body motion level determination unit 14 acquires the acceleration detection signals (acceleration data) from the accelerometer 21 (Step A4). In the pulse measurement device 10, the acquisition of the pulse wave detection signals of Step A2 and acquisition of the acceleration detection signals of Step A3 are executed in parallel. The body motion level determination unit 14 determines a body motion level of the subject based on the acceleration detection signals acquired (Step A5).

Figure 3:
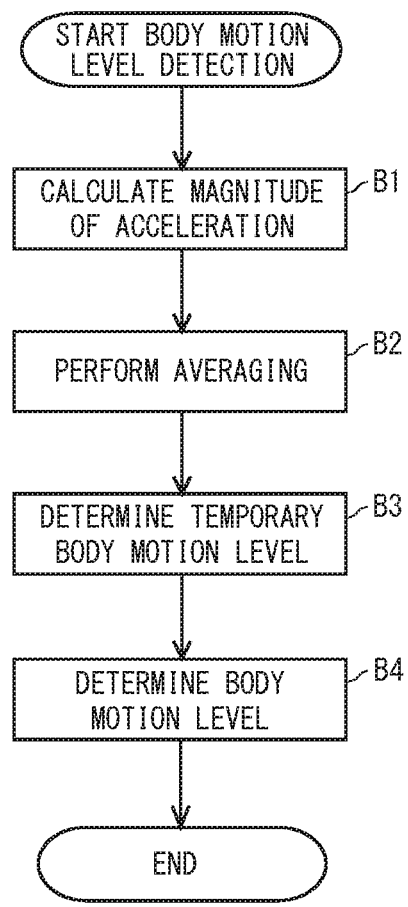
FIG. 3 is a flow chart showing a procedure for determining a body motion level.

FIG. 3 shows a procedure for determining the body motion level. The body motion level determination unit 14 calculates magnitude of the acceleration (Step B1). When the accelerometer 21 outputs acceleration components $\alpha_x$, $\alpha_y$ and $\alpha_z$ for the x axis, the y axis, and the z axis as the acceleration detection signal, the body motion level determination unit 14 calculates square root of a sum of squares of these components as the magnitude of the acceleration. The body motion level determination unit 14 averages the magnitude of the acceleration for multiple times (Step B2). At Step B2, the body motion level determination unit 14 averages, for example, the magnitude of the acceleration detection signals of the accelerometer 21 for 16 times, and calculates an average value of the magnitude of the acceleration during a period in which the acceleration detection signals for the past 16 times are acquired.

The body motion level determination unit 14 determines a temporary body motion level based on the average value of the magnitude of the acceleration calculated at Step B2 (Step B3). For example, the body motion level determination unit 14 uses a plurality of stages of threshold vales, compares the average value of the magnitude of the acceleration with the threshold values, and determines the temporary body motion level in 5 levels of body motion levels 0 to 4 at Step B3. The body motion level determination unit 14 determines that the temporary body motion level is the body motion level 4 which indicates the highest level, for example, when the average value of the magnitude is equal to or greater than the greatest threshold value (a forth threshold value). The body motion level determination unit 14 determines that the temporary body motion level is the body motion level 3 having the higher body motion level next to the body motion level 4, for example, when the average value of the acceleration is equal to or greater than a threshold value (a third threshold value) lower than the fourth threshold value. The body motion level determination unit 14 determines that the temporary body motion level is the body motion level 2, for example, when the average value of the acceleration is equal to or greater than a threshold value (a second threshold value) lower than the third threshold value. The body motion level determination unit 14 determines that the temporary body motion level is the body motion level 1, for example, when the average value of the acceleration is equal to or greater than a threshold value (a first threshold value) lower than the second threshold value. The body motion level determination unit 14 determines that the temporary body motion level is the body motion level 0, for example, when the average value of the acceleration is lower than the first threshold value. It should be noted that the body motion level may express not only the magnitude of the body motion but also types of the body motion and further the types and the magnitude of the body motion.

The body motion determination unit 14 determines (fixes) the body motion level based on the temporary body motion level for multiple times (Step B4). At Step B4, the body motion level determination unit 14 determines the body motion level, for example, based on the result of the determination of the temporary body motion level for 16 times. For example, the body motion level determination unit 14 determines an average value of the result of the determination of the temporary body motion level for 16 times as the body motion level. The body motion determination unit 14 may determine the body motion level based on the other statistic such as a median or a mode instead of determining the average value as the body motion level. The body motion level determination unit 14 determines the body motion level, for example, each time the result of the determination of the temporary body motion level for 16 times are acquired. When the number of the results of the determination of the temporary body motion level is less than 16, for example, immediately after turning on the power supply, the body motion determination unit may determine that the body motion level is the body motion level 0 until a predetermined number of the result of the determination of the temporary body motion level are acquired. The body motion level determination unit 14 informs the peak detection unit 15 of the result of the determination of the body motion level (fixed body motion level).

Referring back to FIG. 2, the peak detection unit 15 sets a searching range of a peak according to the result of the determination of the body motion level of the body motion level determination unit 14 (Step A6). At Step A6, the peak detection unit 15 sets, for example, a frequency position corresponding to a previous result of measurement (pulse measurement value) of a pulse rate as a reference frequency position, and sets the peak searching range with the reference frequency position as a reference. The peak searching range may be defined by a range between a position away from the reference by a lower side difference value (Low) to the lower frequency side and a position away from the reference by a higher side difference value (High) to the higher frequency side.

Figure 4:
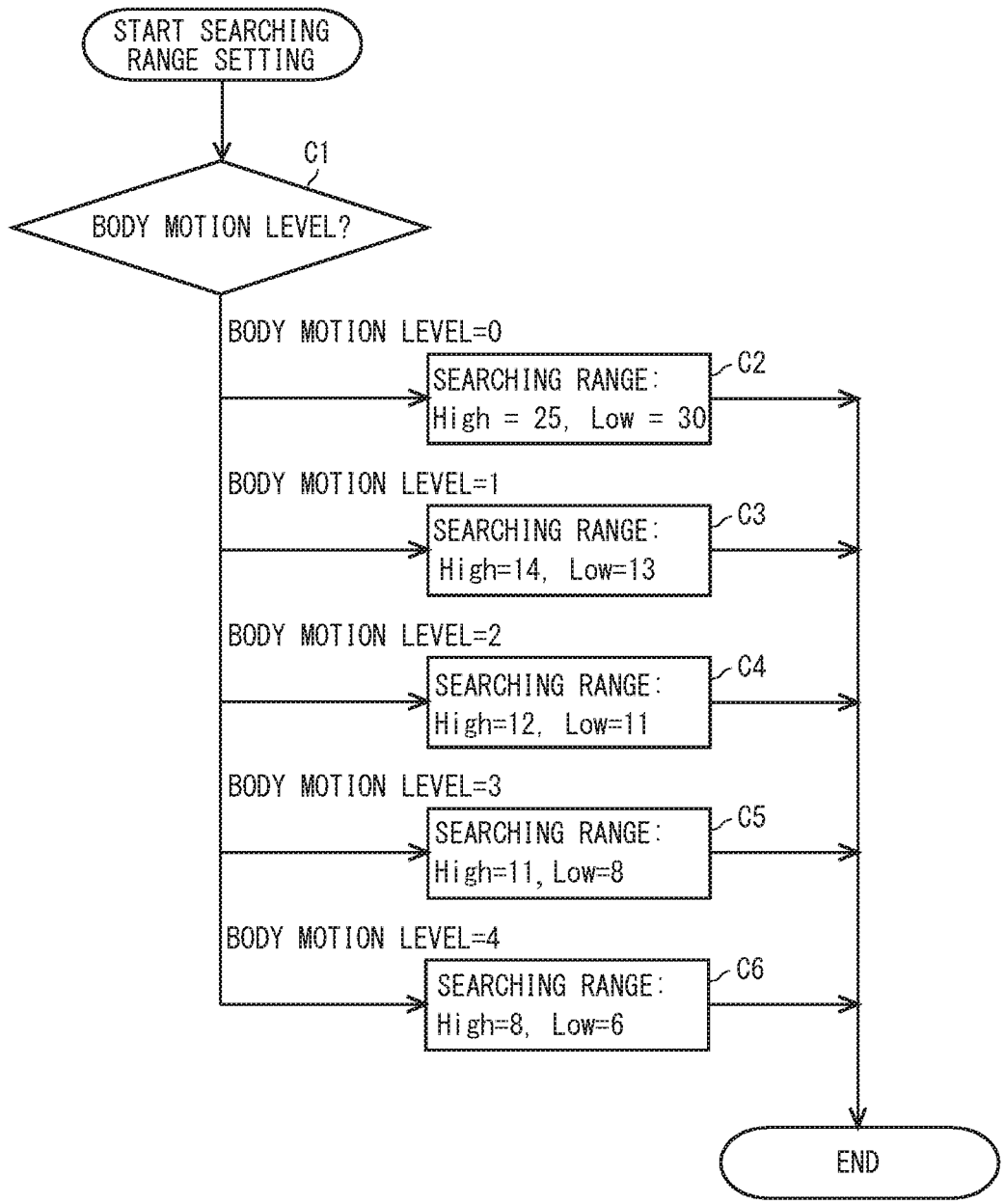
FIG. 4 is a flow chart showing a procedure for setting a peak searching range.

FIG. 4 shows a procedure for setting a peak searching range. The peak detection unit 15 determines the body motion level informed from the body motion level determination unit 14 (Step C1). When the body motion level is '0', the peak detection unit 15 sets the higher side different value (High) to '25' and sets the lower side different value (Low) to '30' (Step C2). When the body motion level is '1', the peak detection unit 15 sets the higher side different value (High) to '14' and sets the lower side different value (Low) to '13' (Step C3).

When the body motion level is '2', the peak detection unit 15 sets the higher side different value (High) to '12' and sets the lower side different value (Low) to '11' (Step C4). When the body motion level is '3', the peak detection unit 15 sets the higher side different value (High) to '11' and sets the lower side different value (Low) to '8' (Step C5). When the body motion level is '4', the peak detection unit 15 sets the higher side different value (High) to '8' and sets the lower side different value (Low) to '6' (Step C6). In this case, it is possible to set the peak searching range according to the body motion level.

Figure 5:
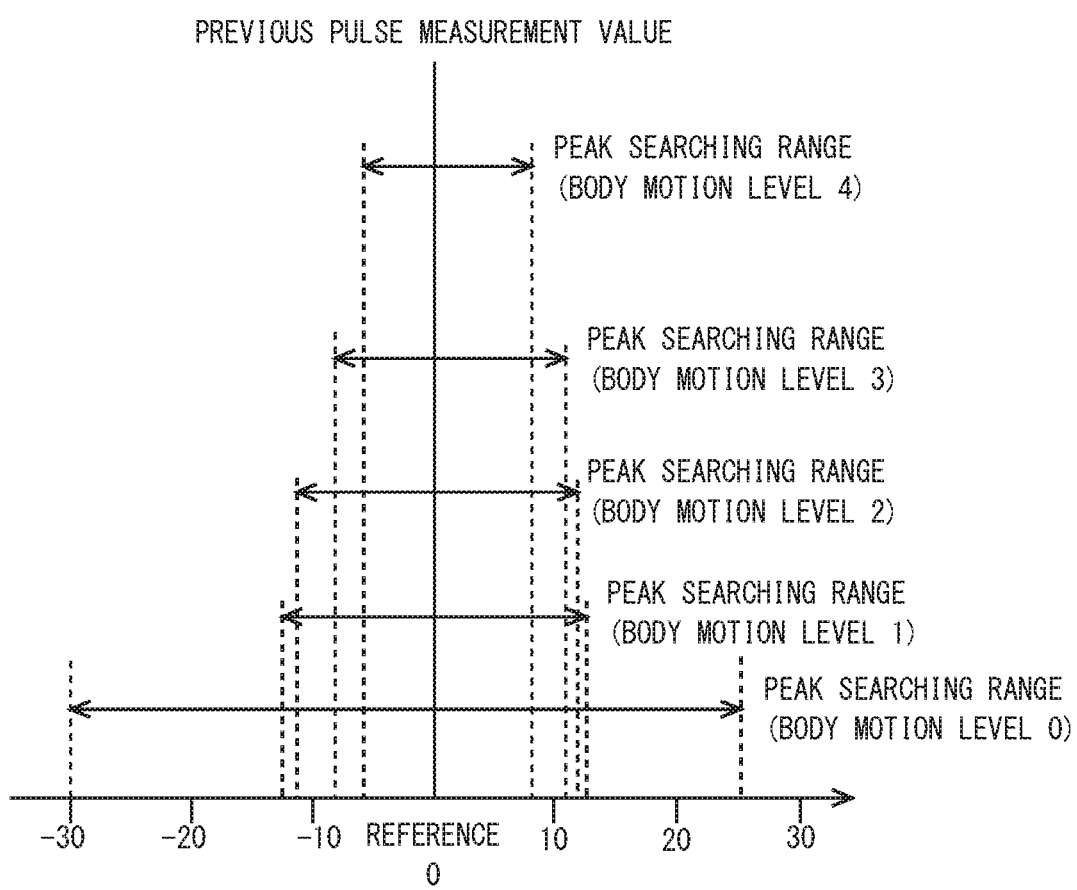
FIG. 5 is a diagram showing the peak searching range for each body motion level.

FIG. 5 shows the peak searching range for each body motion level. The peak detection unit 15 sets a frequency position corresponding to the previous pulse measurement value as the reference frequency position (0), and sets a range between frequency positions away from the reference frequency position by the above-set −Low and +High respectively as the peak searching range. For example, when the previous pulse measurement value is 80 bpm, the peak detection unit 15 sets a range from 50 bpm to 105 bpm as the peak searching range when the body motion level is '0'. The peak detection unit 15 sets a range from 67 bpm to 94 bpm as the peak searching range when the body motion level is '1', and sets a range from 69 bpm to 92 bpm as the peak searching range when the body motion level is '2'. The peak detection unit 15 sets a range from 72 bpm to 91 bpm as the peak searching range when the body motion level is '3', and sets a range from 74 bpm to 88 bpm as the peak searching range when the body motion level is '4'.

It should be noted that, when the body motion levels is '1' or more, the value of High is set to be greater than the value of Low. That is, when a body moves, the peak searching range is set to be wider on the higher side with respect to the previous pulse measurement value and is set to be narrower on the lower side. By setting the peak searching range so, it is possible to make it easier to catch the pulse rise when a body moves. Further, when the body motion level is low, the pulse rate of the subject (user) rises sharply when the user starts to move. In contrast, when the body motion level is high and the pulse rate has already risen to some extent, it is unlikely that the pulse rate further rises sharply from there. Accordingly, the peak searching range is set to be narrower as the body motion level become higher in the present embodiment, whereby the possibility of the erroneous detection can be reduced.

On the other hand, when the body motion level is '0', the value of Low is set to be greater than the value of High. That is, when a body does not move, the peak searching range is set to be wider on the lower side with respect to the previous pulse measurement value and is set to be narrower on the higher side. By setting the peak searching range so, it is possible to handle a drop in the pulse rate after the pulse rate rise, for example, in a situation where the body motion level becomes '0' after a body moves.

Again referring back to FIG. 2, the peak detection unit 15 searches for a peak in the pulse wave frequency signal generated by the frequency analysis unit 13 at Step A3 within the peak searching range set at Step A6 to detect a frequency position at which the spectrum intensity is the maximum within the peak searching range (Step A7). The pulse calculation processing unit 16 converts the frequency position searched for at Step A7 into a pulse value, and output the result of the pulse measurement (Step A8). The pulse calculation processing unit 16 outputs the result of the pulse measurement, for example, to a display unit or another device at Step A8.

Operating Waveform Example

Figure 6A:
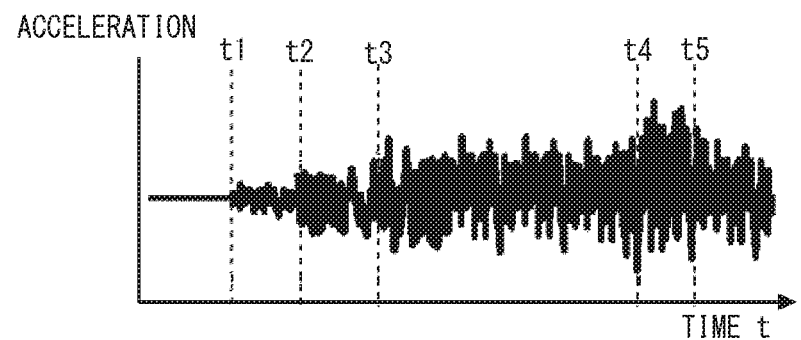
FIG. 6A is a timing chart showing a signal waveform of acceleration detection signals output by an accelerometer.
Figure 6B:
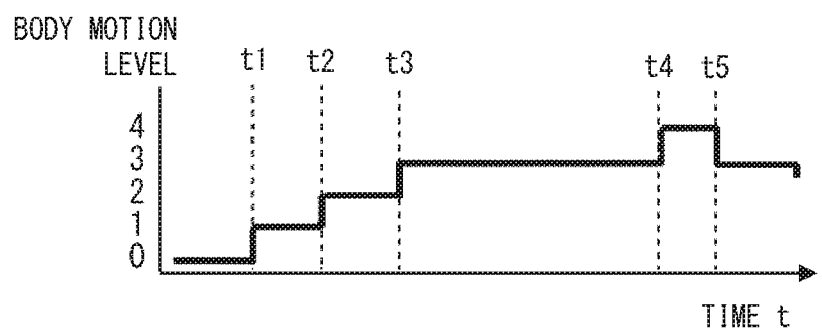
FIG. 6B is a timing chart showing a body motion level determined by a body motion level determination unit.
Figure 6C:
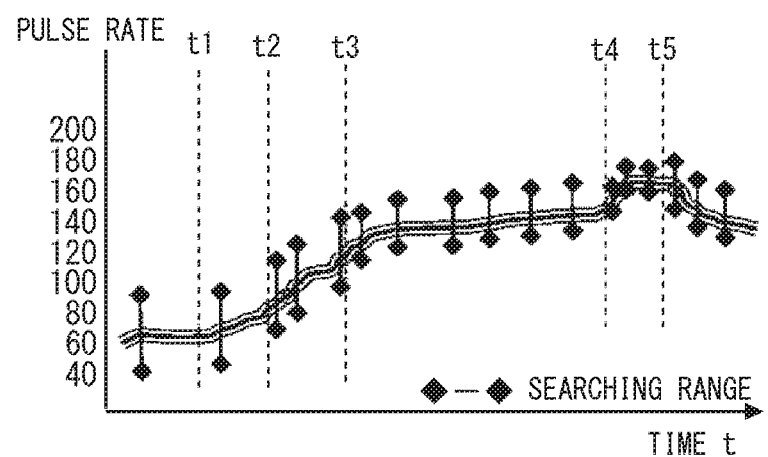
FIG. 6C is a timing chart showing a result of measurement of a pulse rate.

FIG. 6A to FIG. 6C show the operating waveform of each part during the measurement of the pulse rate. In FIG. 6A to FIG. 6C, the horizontal axis represents time respectively. FIG. 6A shows an example of the signal waveform of the acceleration detection signals output by the accelerometer 21. In FIG. 6A, the vertical axis represents the magnitude of the acceleration detection signal. The accelerometer 21 detects the movement (acceleration) of the subject while the measurement device 10 is in operation. The acceleration detection signal output by the accelerometer 21 has smaller magnitude thereof as the motion of the subject becomes smaller, and has greater magnitude thereof as the motion of the subject becomes greater. The magnitude of the acceleration detection signal may vary from moment to moment according to the activity state of the subject.

FIG. 6B shows the body motion level determined by the body motion level determination unit 14. In FIG. 6B, the vertical axis represents the magnitude of the body motion level. The body motion level determination unit 14 determines the body motion level of the subject, for example, according to the procedure shown in FIG. 3. For example, the body motion level determination unit 14 determines the body motion level in 5 levels including resting (level 0), a daily living activity (level 1), walking (level 2), running (level 3), and full-powered running (level 4).

FIG. 6C shows the result of measurement of the pulse rate. In FIG. 6C, the vertical axis represents the pulse value. In FIG. 6C, the peak searching ranges in which the peak of the spectrum intensity is searched for in the pulse wave frequency signal are indicated as well. As shown FIG. 6B, the body motion level of the subject (user) rises, and, in accordance with that, the pulse rate of the user also rises with the lapse of time. The peak detection unit 15 sets the peak searching range with the varying pulse rate as a reference, and detects the peak.

The peak searching range is set according to the body motion level. Prior to time t1, the peak detection unit 15 detects the peak within the peak searching range corresponding to the body motion level '0'. At time t1, when the body motion level determination unit 14 determines that the body motion level is '1', the peak detection unit 15 detects the peak within the peak searching range corresponding to the body motion level '1'. After that, when the body motion level determined by the body motion level determination unit 14 is changed at time t2, t3, t4, and t5, the peak detection unit 15 detects the peak while varying the peak searching range according to the change in the body motion level.

[Summary]

In the present embodiment, the body motion level determination unit 14 determines the body motion level of the subject, and the peak detection 15 detects the peak in the pulse wave frequency signal within the peak searching range determined according to the body motion level. In the present embodiment, since the peak searching range is varied according to the activity state of the subject, it is possible to reduce the erroneous detection of the pulse rate due to body motion noises when a body moves. In addition, when a body moves, by setting the peak searching range to be narrower than that when a body does not move, it is possible to prevent erroneously detecting a peak caused by the body motion frequency as the pulse component. Further, in the present embodiment, the peak searching range is set with the previous pulse measurement value as a reference. Since it is considered that the pulse rate of the subject does not fluctuate greatly from the previous pulse measurement value, by setting the peak searching range with the previous pulse measurement value as a reference, it is possible to reduce the erroneous detection of the pulse rate caused by the body motion noises.

Second Embodiment

Next, a second embodiment is explained. A configuration of a pulse measurement device according to the present embodiment may be the same as the configuration of the pulse measurement device 10 shown in FIG. 1 according to the first embodiment. In the present embodiment, the peak detection unit 15 determines whether the previous pulse measurement value is greater than a predetermined threshold value of not. The peak detection unit 15 adjusts at least one of Low and High of the peak searching range according to the result of the determination. Points other than this point may be the same as the first embodiment.

The peak detection unit 15 carries out the above peak searching range adjustment, for example, when a body moves. The peak detection unit 15 increases the value of High which regulates the higher side searching range with respect to the previous pulse measurement value by a predetermined value (first predetermined value), for example, when the body motion determined by the body motion level determination unit 14 is '1' or more indicating that a body moves and it is determined that the previous pulse measurement value is greater than the predetermined threshold value. The peak detection unit 15 may increase the value of High by a predetermined value (second predetermined value) lower than the first predetermined value, for example, when the body motion level determined by the body motion level determination unit 14 is '1' or more indicating that a body moves and it is determined that the previous pulse measurement value is not greater than the predetermined threshold value.

The peak detection unit 15 may decrease the value of Low by an adjustment value (first adjustment value) corresponding to the difference between the previous pulse measurement value and the predetermined threshold value, for example, when the body motion level determined by the body motion level determination unit 14 is '1' or more indicating that a body moves and it is determined that the previous pulse measurement value is greater than the predetermined threshold value. The peak detection unit 15 may increase the value of Low by an adjustment value (second adjustment value) when the body motion level is a body motion level associated with no body motion and it is determined that the previous pulse measurement value is not greater than the predetermined threshold value.

[Operation Procedure]

Figure 7:
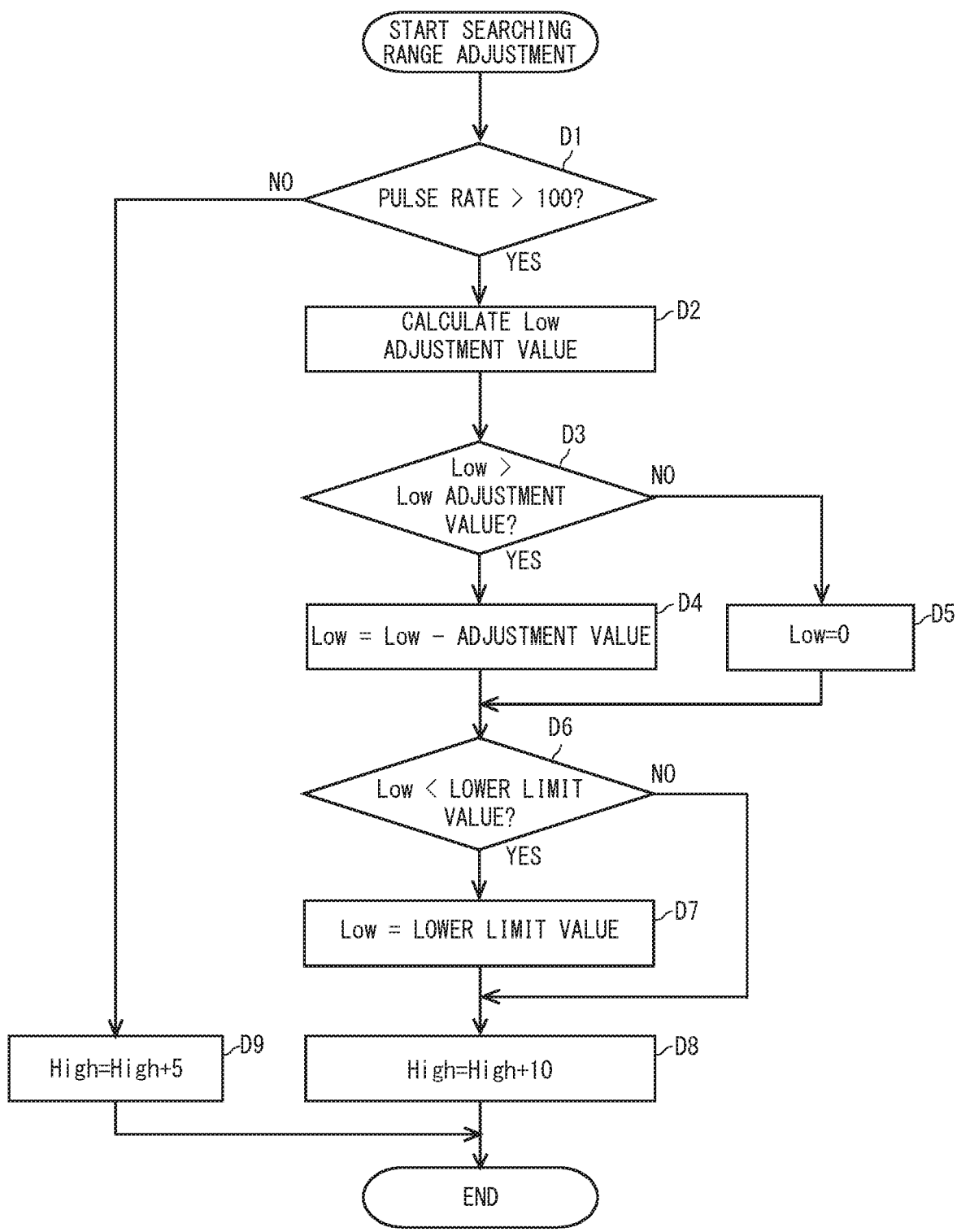
FIG. 7 is a flow chart showing a procedure for adjusting a peak searching range in a second embodiment.

FIG. 7 shows a procedure for adjusting the peak searching range. It is assumed that the adjustment of the peak searching range is carried out, for example, after the peak searching range is set at Step A6 of FIG. 2 when the body motion level determined at Step A5 is '1' or more. The peak detection unit 15 determines whether the previous pulse measurement value is greater than a predetermined threshold value or not (Step D1). The predetermined threshold value is set, for example, to a pulse value indicating a boundary between a pulse rate of the user in an activity state and a pulse rate in a non-activity state. At Step D1, the peak detection unit 15 determines, for example, the previous pulse measurement value is greater than 100 bpm or not.

When the peak detection unit 15 determines that the previous pulse measurement value is greater than 100 bpm at Step D1, the peak detection unit 15 calculates a Low adjustment value based on the different between the previous pulse measurement value and the predetermined threshold vale (Step D2). For example, the peak detection unit 15 calculates the Low adjustment value according to the formula set forth below at Step D2.

Low adjustment value=(previous pulse measurement value−100)/2

The peak detection unit 15 compares the value of Low determined at Step A6 of FIG. 2 with the Low adjustment value calculated at Step D2 to determine whether the value of Low is greater than the Low adjustment value or not (Step D3). When the peak detection unit 15 determines that the value of Low is greater than the Low adjustment value, the peak detection unit 15 decreases the value of Low by the Low adjustment value (Step D4). That is, the peak detection unit 15 sets the 'Low-Low adjustment value' to the value of Low after the adjustment. When the peak detection unit 15 determines that the value of Low is not greater than the Low adjustment value at Step D3, the peak detection unit 15 sets the value of Low to '0' (Step D5).

The peak detection unit 15 determines whether the value of Low is smaller than a predetermined lower limit value or not (Step D6). For example, the peak detection unit 15 determines whether the value of Low is smaller than '6' or not at Step D6. The peak detection unit 15 determines that the value of Low is smaller than the lower side limit value at Step D6 when the value of Low adjusted at Step D4 is smaller than '6'. The peak detection unit 15 determines that the value of Low is smaller than the lower limit value at Step D6 as well when the value of Low is set to '0' at Step D5.

The peak detection unit 15 sets the value of Low to the lower limit value when it is determined that the value of Low is smaller than the lower limit value at Step D6 (Step D7). By doing so, the peak searching range includes at least a range from the previous pulse measurement value to a frequency lower than the previous pulse measurement value by the lower limit value. When it is determined that the value of Low is not smaller than the lower limit value at Step D6, the correction of the value of Low is not carried out.

The peak detection unit 15 sets a value obtained by adding a predetermined value to the value of High determined at Step A6 of FIG. 2 as the value of High after the adjustment (Step D8). The peak detection unit 15 sets a value obtained by adding '10' to the value of High as the value of High after the adjustment at Step D8. When the peak detection unit 15 determines that the previous pulse measurement value is not greater than the predetermined value at Step D1, the peak detection unit 15 sets a value obtained by adding another predetermined value to the value of High determined at Step A6 of FIG. 2 as the value of High after the adjustment (Step D9). The peak detection unit 15 sets, for example, a value obtained by adding '5' to the value of High as the value of High after the adjustment at Step D9.

By carrying out the above procedure, when the body motion level is '1' or more and, for example, the previous pulse measurement value is over 100 bpm, the peak searching range is expanded at the higher frequency side with respect to the previous measurement value, for example, by '10' comparing to a case where the adjustment of the peak searching range is not carried out. Further, when the body motion level is '1' ore more and, for example, the previous pulse measurement value is not over 100 bpm, the peak searching range is expanded at the higher frequency side with respect to the previous measurement value, for example, by '5' comparing to a case where the adjustment of the peak searching range is not carried out. As for the lower frequency side with respect to the previous pulse measurement value, when the body motion level is '1' or more and, for example, the previous pulse measurement value is not over 100 bpm, the peak searching range is tighten by an adjustment amount corresponding to the difference between, for example, 100 bpm and the previous pulse measurement value, with, for example '6' as the lower limit value.

Operation Wave Example

Figure 8A:
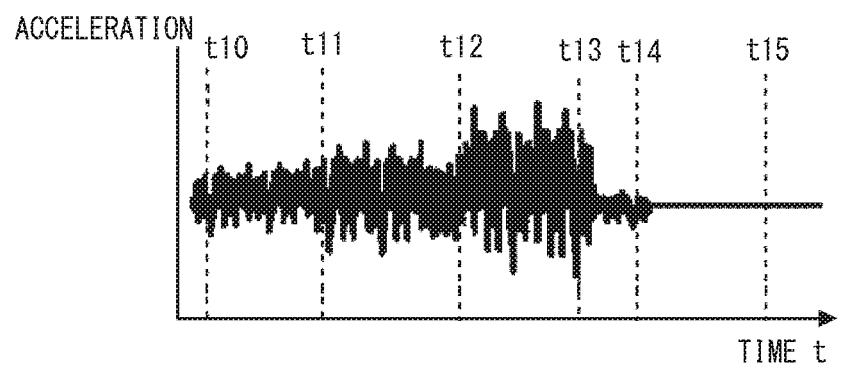
FIG. 8A is a timing chart showing a signal waveform of acceleration detection signals output by an accelerometer.
Figure 8B:
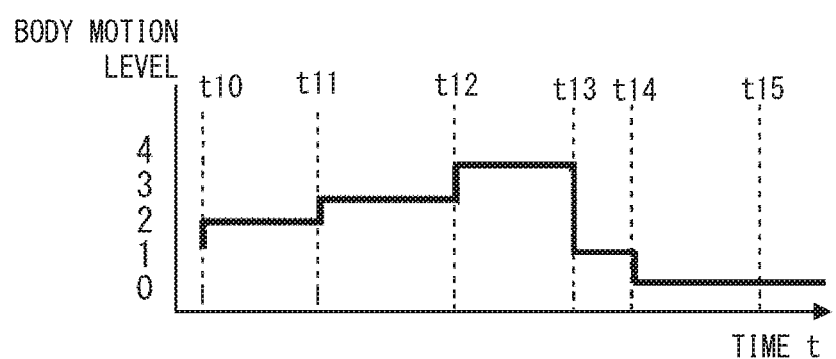
FIG. 8B is a timing chart showing a body motion level determined by a body motion level determination unit.
Figure 8C:
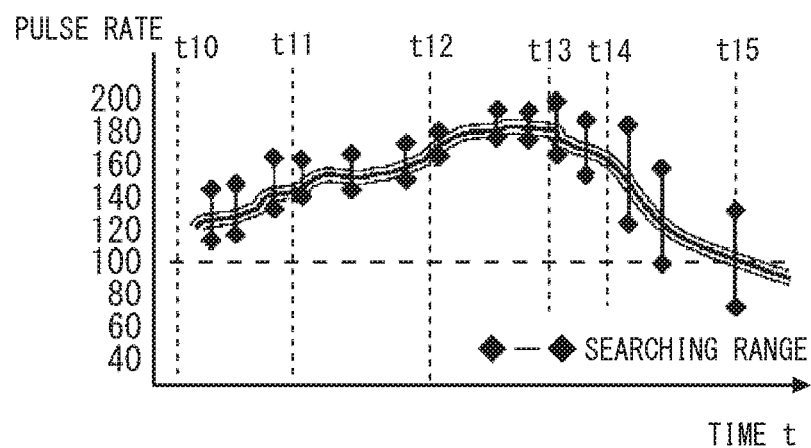
FIG. 8C is a timing chart showing a result of measurement of a pulse rate.

FIG. 8A to FIG. 8C show the operating waveform of each part during the measurement of the pulse rate. In FIG. 8A to FIG. 8C, the horizontal axis represents time respectively. FIG. 8A shows an example of the signal waveform of the acceleration detection signals output by the accelerometer 21, similar to FIG. 6A. FIG. 8B shows the body motion level determined by the body motion level determination unit 14, similar to FIG. 6B. FIG. 8C shows the result of measurement of the pulse rate, similar to FIG. 6C. In FIG. 8C, the peak searching ranges in which the peak of the spectrum intensity is searched for in the pulse wave frequency signal are indicated as well.

At time t10, the user is already in an activity level, and the measurement value of the pulse rate is over 100 bpm. In this case, the peak detection unit 15 detects a peak within the peak searching range adjusted by the procedure shown in FIG. 7. When the body motion level of the user changes at time t11, t12, and t13, the peak detection unit 15 detects a peak within the peak searching range obtained by adjusting the peak searching range corresponding to the body motion level by the procedure shown in FIG. 7. At time t14, when it is determined that the body motion level is '0', the peak detection unit 15 ends the adjustment of the peak searching range.

It is considered that the pulse rate of the user whose body is moving decreases sharply after he/she stops his/her movement. The peak detection unit 15 may adjust the peak searching range by a procedure other than the procedure shown in FIG. 7 to expand the peak searching range at the lower frequency side with respect to the previous pulse measurement value when it is determined that the body motion level is '0' and the previous pulse measurement value is over 100 bpm. In this case, it is possible to deal with the sudden decrease of the pulse rate. The peak detection unit 15 may detect the peak within the normal peak searching range after the pulse rate becomes 100 bpm or less at time t15.

[Summary]

In the present embodiment, the peak detection unit 15 adjusts at least one of Low and High of the peak searching range according to whether or not the pulse measurement value is, for example, 100 or more when a body moves. By expanding the peak searching range at the higher frequency side when the pulse rate of the user becomes high to a certain degree, the peak detection unit 15 can detect the peak while following the pulse rate rise during the exercise.

Third Embodiment

Figure 9:
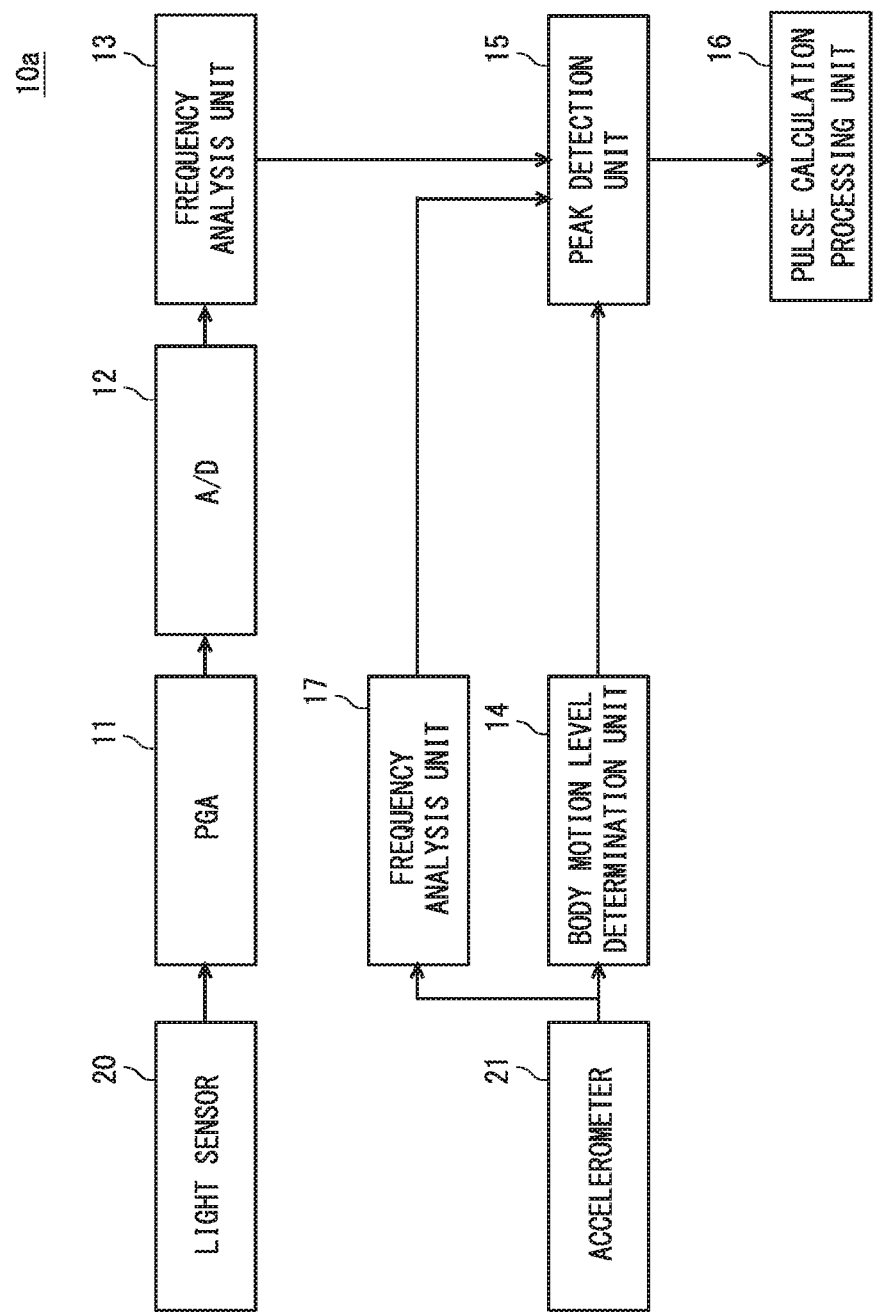
FIG. 9 is a block diagram showing a pulse measurement device according to a third embodiment.

Next, a third embodiment is explained. FIG. 9 shows a pulse measurement device according to the third embodiment. The pulse measurement device 10a according to the present embodiment further comprises a frequency analysis unit 17 in addition to the configuration of the pulse measurement device 10 shown in FIG. 1 according to the first embodiment. The frequency analysis unit 17 generates an acceleration frequency information signal by converting the acceleration detection signals which are time domain signals into a frequency domain signal. In the present embodiment, the peak detection unit 15 modifies the pulse wave frequency signal generated by the frequency analysis unit 13 using the acceleration frequency information signal generated by the frequency analysis unit 17 when the body motion level determined by the body motion level determination unit 14 indicates that a body moves. Points other than the above point may be the same as the first embodiment or the second embodiment.

The frequency analysis unit 17 is an acceleration frequency information generation module, and performs Fast Fourier Transform on the acceleration detection signals to convert the acceleration detection signals which are time domain signals into the acceleration frequency information signal which is a frequency domain signal. The frequency analysis unit 17 periodically acquires the acceleration detection signals from the accelerometer 21. The frequency analysis unit 17 performs Fast Fourier Transform, for example, each time the acceleration detection signals of data points required for Fast Fourier Transform are acquired. The frequency analysis unit 17 performs Fast Fourier Transform, for example, when the body motion level determined by the body motion level determination unit 14 indicates that a body moves. The frequency analysis unit 17 can not perform Fast Fourier Transform when the body motion level determined by the body motion level determination unit 14 indicates no body motion.

In the present embodiment, the peak detection unit 15 detects a peak of spectrum intensity in the acceleration frequency information signal, in addition to the detection of the peak in the pulse wave frequency signal. The peak detection unit 15 compares the frequency position of peak of the pulse wave frequency signal with the frequency position of the peak of the acceleration frequency information signal. When the compared frequency positions are matched, the peak detection unit 15 attenuates spectrum intensity of the pulse wave frequency signal at that frequency position. The peak detection unit 15 attenuates the spectrum intensity of the pulse wave frequency signal by an attenuation amount in accordance with spectrum intensity of the acceleration frequency information signal at the frequency position at which the peaks are matched. The peak detection unit 15 detects the peak from the pulse wave frequency signal, the spectrum intensity of which is attenuated. In the following description, the attenuation of the spectrum intensity of the pulse wave frequency signal as such may be referred as a body motion noise cancelling process.

Here, in the present embodiment, it is assumed that the signal sampling number per unit time of the pulse wave detection signals on which Fast Fourier Transform is to be performed by the frequency analysis unit 13 and the signal sampling number per unit time of the acceleration detection signals on which Fast Fourier Transform is to be performed by the frequency analysis unit 17 are the same. For example, the AD converter 12 carrying out the AD conversion of the pulse wave detection signals and an AD converter included in the accelerometer 21 carries out sampling of signals at the same sampling rate.

Further, in the present embodiment, it is assumed that data points of the pulse wave detection signals on which the frequency analysis unit 13 performs Fast Fourier Transform and data points of the acceleration detection signals on which the frequency analysis unit 17 performs Fast Fourier Transform are the same. In the present embodiment, the frequency analysis unit 17 performs Fourier Transform on the acceleration detection signals acquired within the same period as the acquisition period of the pulse wave detection signals on which the frequency analysis unit 13 performs Fast Fourier Transform. In this way, it is possible to compare the both results of the frequency analyses in the same period. In addition, it is possible to match the frequency axes of the pulse wave frequency signal and the acceleration frequency information signal, whereby it is easy to determine whether the peak positions are matched or not.

[Operation Procedure]

Figure 10:
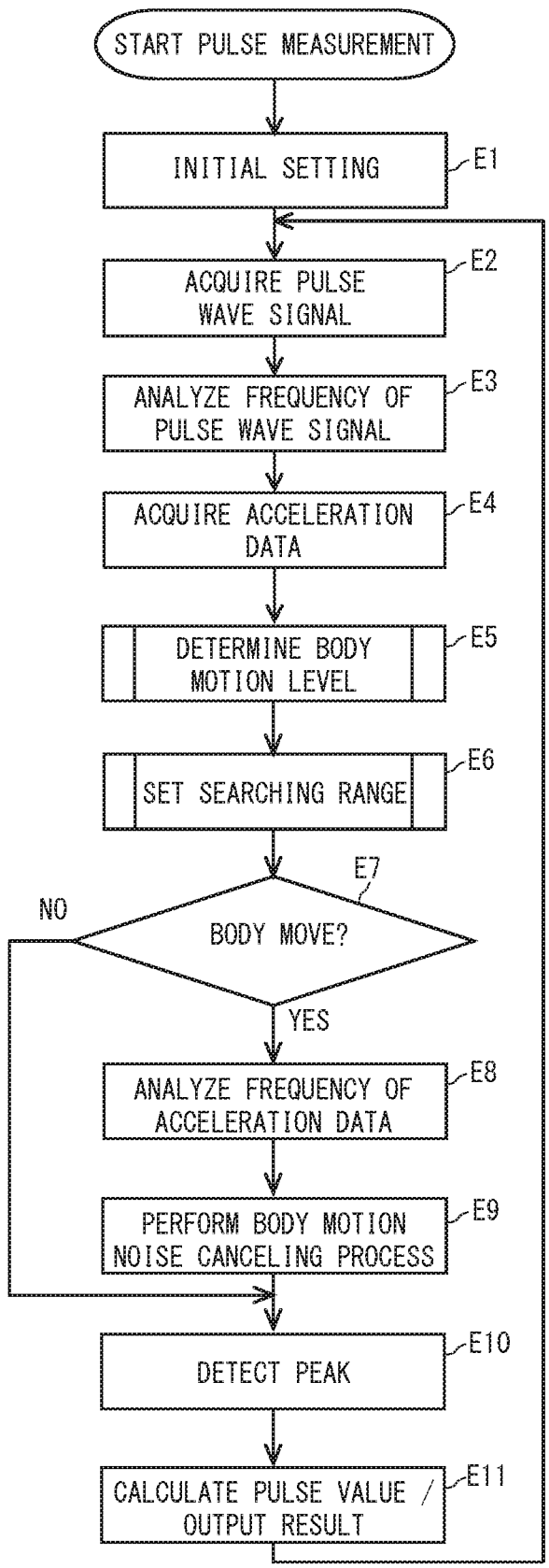
FIG. 10 is a flow chart showing a procedure for measuring a pulse in a third embodiment.

FIG. 10 shows a procedure for measuring the pulse. For example, prior to a measurement of the pulse rate, the pulse measurement device 10a carries out initial setting (Step E1). The frequency analysis unit 13 acquires the pulse wave detection signals via the PGA 11 and the AD converter 12 (Step E2). The frequency analysis unit 13 performs, for example, Fast Fourier Transform on the acquired pulse wave detection signals to convert the pulse wave detection signals into a pulse wave frequency signal in the frequency domain (Step E3). The frequency analysis unit 13 executes Step E3, for example, each time the pulse wave detection signals of data points required for Fast Fourier Transform are acquired.

On the other hand, for example, the accelerometer 21 continuously outputs acceleration detection signals. The body motion level determination unit 14 acquires the acceleration detection signals (acceleration data) from the accelerometer 21 (Step E4). In the pulse measurement device 10a, the acquisition of the pulse wave detection signals of Step E2 and acquisition of the acceleration detection signals of Step E3 are executed in parallel. The body motion level determination unit 14 determines a body motion level of the subject based on the acceleration detection signals acquired (Step E5). The peak detection unit 15 sets a searching range of a peak according to the result of the determination of the body motion level of the body motion level determination unit 14 (Step E6). Note that Steps E1 to E6 may be the same as Steps A1 to A6 of FIG. 2.

The frequency analysis unit 17 determines whether or not the body motion level determination unit 14 determines that a body moves (Step E7). When it is determined that the body motion level determination unit 14 determines that a body moves, the frequency analysis unit 17 performs Fast Fourier Transform on the acceleration detection signals to generate an acceleration frequency information signal (Step E8). The peak detection unit 15 acquires the acceleration frequency information signal from the frequency analysis unit 17 and carries out a body motion cancelling process using the pulse wave frequency signal and the acceleration frequency information signal (Step E9).

In the body motion cancelling process of Step E9, the peak detection unit 15 detects a peak of the spectrum intensity in the acceleration frequency information signal, for example, within the peak searching range set at Step E6. For example, the peak detection unit 15 detects, within the peak searching range, peaks of the spectrum intensity in the acceleration frequency information signal by a predetermined number in a descending order of the spectrum intensity. For example, the peak detection unit 15 detects three peaks of the acceleration frequency information signal in a descending order of the spectrum intensity within the peak searching range. The peak detection unit 15 determines whether each of frequency positions of the peaks detected by the predetermined number is matched the frequency position of the peak of the pulse wave frequency signal. When the frequency positions are matched, the peak detection unit 15 may attenuates the spectrum intensity of the pulse wave frequency signal.

When it is determined that the body motion level determination unit 14 does not determine that a body move, the frequency analysis unit 17 does not generate the acceleration frequency information signal. Alternative to this, the frequency analysis unit 17 may always generate the acceleration frequency information signal, and the peak detection unit 15 may acquire the acceleration frequency information signal when it is determined that a body moves. When the acceleration frequency information signal is generated in the frequency analysis unit 17 only the case where it is determined that a body moves in the body motion level determination unit 14, it is possible to reduce an unnecessary frequency analysis, and this can contributes low power consumption of the pulse measurement device 10a.

The peak detection unit 15 searches for a peak in the pulse wave frequency signal generated by the frequency analysis unit 13 at Step E3 or the pulse wave frequency signal on which the body motion noise cancelling process is performed at Step E9, within the peak searching range set at Step E6 to detect a frequency position at which the spectrum intensity is the maximum within the peak searching range (Step E10). The pulse calculation processing unit 16 converts the frequency position searched for at Step E10 into a pulse value, and output the result of the pulse measurement (Step E11). Note that Steps E10 and E11 may be the same as Steps A7 and A8 of FIG. 2.

[Summary]

In the present embodiment, the frequency analysis unit 17 converts the acceleration detection signals which are time domain signals into the acceleration frequency information signal which is a frequency domain signal. By performing the body motion noise cancelling process using the acceleration frequency information signal, it is possible to attenuate body motion components included in the pulse wave frequency signal. When it is determined that a body moves, by detecting the peak from the pulse wave frequency signal on which the body motion noise cancelling process is performed, it is possible to measure the pulse rate correctly even in cases where a body motion noise component is present in the vicinity of the pulse component in the pulse wave frequency signal. When the frequency analyses are carried out at the same sampling rate and on the same data points in the frequency analysis unit 13 and the frequency analysis unit 17, it is possible to improve the accuracy of the body motion noise cancelling process.

It should be noted that, in each of the above-described embodiments, although an example where the light sensor 20 is used for the measurement of the pulse rate, the present disclosure is not limited thereto. The pulse sensor used for measuring the pulse rate is not limited to light sensor 20. It is possible to use another sensor capable of outputting detection signals of the pulse wave of the subject, for example, a pressure sensor as the pulse sensor.

While the invention has been described in terms of several embodiments, those skilled in the art will recognize that the invention can be practiced with various modifications within the spirit and scope of the appended claims and the invention is not limited to the examples described above.

Two or more of the above described embodiments can be combined as desirable by one of ordinary skill in the art.

Further, the scope of the claims is not limited by the embodiments described above.

Furthermore, it is noted that, Applicant's intent is to encompass equivalents of all claim elements, even if amended later during prosecution.

What is claimed is:

1. A pulse measurement device comprising:
   a pulse sensor configured to detect pulse waves of a subject and generate a pulse wave detection signal based on the detected pulse waves; and
   a central processing unit (CPU) configured to perform functions of:
      a pulse wave frequency information generation module configured to generate a pulse wave frequency signal by converting the pulse wave detection signal into a frequency domain signal from a time domain signal;
      a peak detection module configured to detect a peak of a spectrum in the pulse wave frequency signal;
      a pulse information generation module configured to generate pulse information based on a frequency position of the peak detected by the peak detection module;
      an accelerometer configured to detect acceleration of the subject and output an acceleration detection signal; and
      a body motion level determination module configured to determine a body motion level of the subject based on the acceleration detection signal,
   wherein the peak detection module 1) sets a reference frequency position at a frequency position corresponding to a previous result of measurement of a pulse rate, 2) sets a peak searching range based on the reference frequency position, and 3) searches for the peak from within the peak searching range,
   wherein a lower limit of the peak searching range is set at a position that differs from the reference frequency position by a first value,
   wherein an upper limit of the peak searching range is set at a position that differs from the reference frequency position by a second value,
   wherein the peak detection module varies the peak searching range by varying, based on the body motion level, the first value for setting the lower limit and the second value for setting the upper limit, and
   wherein the peak detection module determines whether the previous result of measurement of the pulse rate is greater than a predetermined threshold value or not, and adjusts at least one of the lower side difference value and the higher side difference value according to a result of a determination.

2. The pulse measurement device according to claim 1, wherein the peak detection module searches for the peak within the peak searching range defined for each of the body motion levels.

3. The pulse measurement device according to claim 2, wherein the body motion level is determined to be higher as a body motion of the subject becomes greater, and the peak searching range is set to be narrower as the body motion level becomes higher.

4. The pulse measurement device according to claim 1, wherein the peak detection module increases the second value by a first predetermined value when the body motion level determined by the body motion level determination module indicates that the body motion of the subject and the peak detection module determines that the previous result of measurement of the pulse rate is greater than the predetermined threshold value.

5. The pulse measurement device according to claim 4, wherein the peak detection module increases the second value by a second predetermined value that is lower than the first predetermined value when the body motion level determined by the body motion level determination module indicates that the body motion of the subject and the peak detection module determines that the previous result of measurement of the pulse rate is not greater than the predetermined threshold value.

6. The pulse measurement device according to claim 4, wherein the peak detection module decreases the first value by a first adjustment value corresponding to a difference between the previous result of measurement of the pulse rate and the predetermined threshold value when the body motion level determined by the body motion level determination module indicates that the body motion of the subject and the peak detection module determines that the previous result of measurement of the pulse rate is greater than the predetermined value.

7. The pulse measurement device according to claim 4, wherein the peak detection module increases the first value by a second adjustment value when the body motion level is a body motion level associated with no body motion and the peak detection module determines that the previous result of measurement of the pulse rate is not greater than the predetermined threshold value.

8. The pulse measurement device according to claim 1, wherein the CPU further performs functions of an acceleration frequency information generation module configured to generate an acceleration frequency information signal by converting the acceleration detection signal into a frequency domain signal from a time domain signal,
wherein the peak detection module further detects a peak of a spectrum in the acceleration frequency information signal,
wherein, when the frequency position at which the spectrum in the pulse wave frequency signal forms the peak and a frequency position at which the spectrum in the acceleration frequency information signal forms a peak match each other, the peak detection module 1) attenuates spectrum intensity of the pulse wave frequency signal at a position where the frequency positions match, and 2) detects the peak from the pulse wave frequency signal, the spectrum intensity of which is attenuated.

9. The pulse measurement device according to claim 8, wherein the peak detection module attenuates the spectrum intensity of the pulse wave frequency signal at a position where the frequency positions match by an attenuation amount in accordance with spectrum intensity of the acceleration frequency information signal at a position where the frequency positions match.

10. The pulse measurement device according to claim 8, wherein the peak detection module detects the peak of the spectrum in the acceleration frequency information signal within the peak searching range.

11. The pulse measurement device according to claim 10, wherein the peak detection module detects, within the peak searching range, peaks of the spectrum in the acceleration frequency information signal by a predetermined number in a descending order of the spectrum intensity.

12. The pulse measurement device according to claim 8, wherein a number of signal samples per unit time of the pulse wave detection signal equals to a number of signal samples per unit time of the acceleration detection signal, and a number of data points of the pulse wave detection signal from which the pulse wave frequency information generation module generates the pulse wave frequency signal equals to a number of data points of the acceleration detection signal from which the acceleration frequency information generation module generates the acceleration frequency information signal.

13. The pulse measurement device according to claim 8, wherein the acceleration frequency information generation module generates the acceleration frequency information signal when the body motion level determined by the body motion level determination module indicates that the body motion of the subject.

14. The pulse measurement device according to claim 1, wherein the body motion level determination module calculates an average value of magnitude of the acceleration detection signal within a predetermined period, determines a temporary body motion level based on the average value, and determines the body motion level based on the temporary body motion level for multiple times.

15. The pulse measurement device according to claim 14, wherein the body motion level determination module sets an average value of the temporary body motion level for multiple times as a value of the body motion level.

16. A pule measurement method comprising:
   acquiring, from a pulse sensor, a pulse wave detection signal generated based on pulse waves of a subject detected by the pulse sensor;
   generating a pulse wave frequency signal by converting the pulse wave detection signal into a frequency domain signal from a time domain signal;
   acquiring an acceleration detection signal indicating acceleration of the subject
   determining a body motion level of the subject based on 1) calculating an average value of magnitude of the acceleration detection signal within a predetermined period, 2) determining a temporary body motion level based on the average value, and 3) determining the body motion level based on the temporary body motion level for multiple times;
   setting a peak searching range by 1) setting a reference frequency position is set at a frequency position corresponding to a previous result of measurement of a pulse rate, 2) setting a lower limit of the peak searching range at a position that differs from the reference frequency position by a first value, and 3) setting an upper limit of the peak searching range at a position that differs from the reference frequency position by a second value, wherein the peak searching range varies based on varying the first value for setting the lower limit and the second value for setting the upper limit according to the body motion level;
   searching for a peak of a spectrum in the pulse wave frequency signal within a searching range varying based on the body motion level; and
   generating pulse information based on a frequency position of the peak detected by searching for the peak.

17. A non-transitory computer readable medium storing a program which causes a processor to execute steps of:
   acquiring, from a pulse sensor, a pulse wave detection signal generated based on pulse waves of a subject detected by the pulse sensor;

generating a pulse wave frequency signal by converting the pulse wave detection signal into a frequency domain signal from time domain signal;

acquiring an acceleration detection signal indicating acceleration of the subject;

determining a body motion level of the subject based on the acceleration detection signal;

setting a peak searching range by 1) setting a reference frequency position is set at a frequency position corresponding to a previous result of measurement of a pulse rate, 2) setting a lower limit of the peak searching range at a position that differs from the reference frequency position by a first value, and 3) setting an upper limit of the peak searching range at a position that differs from the reference frequency position by a second value, wherein the peak searching range varies based on varying the first value for setting the lower limit and the second value for setting the upper limit according to the body motion level;

searching for a peak of a spectrum in the pulse wave frequency signal within a searching range varying based on the body motion level;

generating pulse information based on a frequency position of the peak detected by searching for the peak;

determining whether the previous result of measurement of the pulse rate is greater than a predetermined threshold value; and adjusting at least one of the lower side difference value and the higher side difference value according to a result of a determination.

* * * * *